(12) United States Patent
Viola et al.

(10) Patent No.: US 12,176,079 B2
(45) Date of Patent: Dec. 24, 2024

(54) METHOD, SYSTEM, AND DEVICE FOR PROVIDING ASSISTANCE TO PATIENTS WITH COMMUNICATION AND MEMORY IMPAIRMENT

(71) Applicant: HCL Technologies Italy S.p.A., Vimodrone (IT)

(72) Inventors: Raffaella Viola, Rome (IT); Giuseppe Longobardi, Rome (IT)

(73) Assignee: HCL Technologies Italy S.p.A., Vimodrone (MI) (IT)

( * ) Notice: Subject to any disclaimer, the term of this patent is extended or adjusted under 35 U.S.C. 154(b) by 434 days.

(21) Appl. No.: 16/988,146

(22) Filed: Aug. 7, 2020

(65) Prior Publication Data
US 2022/0044771 A1     Feb. 10, 2022

(51) Int. Cl.
*G16H 10/60*     (2018.01)
*G06F 16/22*     (2019.01)
(Continued)

(52) U.S. Cl.
CPC ......... *G16H 10/60* (2018.01); *G06F 16/2246* (2019.01); *G06F 16/24564* (2019.01); *G06F 16/284* (2019.01); *G16H 40/67* (2018.01)

(58) Field of Classification Search
CPC .... A61B 2034/2065; A61B 2034/2055; A61B 2090/371; A61B 2034/2057;
(Continued)

(56) References Cited

U.S. PATENT DOCUMENTS 9,020,529 B2     4/2015 Chen
9,251,713 B1 *   2/2016 Giovanniello ........... G09B 7/00
(Continued)

FOREIGN PATENT DOCUMENTS

CN     100595787 C     3/2010
CN     107438398 A     12/2017
(Continued)

OTHER PUBLICATIONS

Valero Má, Bravo J, Chamizo JM, López-de-Ipiña D. Integration of multisensor hybrid reasoners to support personal autonomy in the smart home. Sensors (Basel). 2014;14(9):17313-17330. Published Sep. 17, 2014. doi: 10.3390/s140917313 (Year: 2014).*
(Continued)

*Primary Examiner* — Joseph D Burgess
(74) *Attorney, Agent, or Firm* — Kendal M. Sheets

(57) ABSTRACT

A method, system, and device for providing assistance to patients with communication and memory impairment is disclosed. In some embodiments, the method includes creating a database comprising a plurality of information elements structured as a dependency tree, based on a first set of information corresponding to a plurality of events associated with a patient. The method further includes acquiring a second set of information associated with the patient in real time, matching the second set of information with each of the plurality of events in the database and with at least one information element associated with the at least one matching event, comparing the second set of information with the set of matching information elements to identify at least one discrepancy, and prompting the patient to perform at least one predetermined action in response to identifying the at least one discrepancy.

17 Claims, 10 Drawing Sheets

(51) Int. Cl.
*G06F 16/2455* (2019.01)
*G06F 16/28* (2019.01)
*G16H 40/67* (2018.01)

(58) Field of Classification Search
CPC ........ A61B 2034/105; A61B 2090/364; A61B 5/1124; A61B 2017/00207; A61B 5/4088; A61B 5/4082; A61B 5/4076; G16H 30/40; G16H 15/00; G16H 30/20; G16H 10/60; G16H 20/30; G16H 20/00; G16H 80/00; G16H 20/70; G16H 40/67; G16H 20/10
See application file for complete search history.

(56) References Cited

U.S. PATENT DOCUMENTS

| | | | |
|---|---|---|---|
| 9,819,754 B2 | 11/2017 | Park et al. | |
| 10,133,938 B2 | 11/2018 | Kim et al. | |
| 10,405,786 B2 | 9/2019 | Sahin | |
| 2006/0190440 A1 | 8/2006 | Horvitz et al. | |
| 2007/0276270 A1* | 11/2007 | Tran | A61B 5/0022 600/508 |
| 2014/0153794 A1* | 6/2014 | Varaklis | G06T 7/0012 382/128 |
| 2014/0214448 A1* | 7/2014 | Hanina | G16H 10/60 705/2 |
| 2015/0223731 A1* | 8/2015 | Sahin | A61B 5/16 600/595 |
| 2016/0027278 A1* | 1/2016 | McIntosh | G08B 21/0423 715/741 |
| 2016/0253910 A1* | 9/2016 | Fisher | G09B 5/02 434/236 |
| 2016/0262660 A1* | 9/2016 | Gettelman | G06V 40/23 |

FOREIGN PATENT DOCUMENTS

| | | |
|---|---|---|
| CN | 110838357 A | 2/2020 |
| EP | 3338248 B1 | 11/2019 |

OTHER PUBLICATIONS

A. Araújo et al., "A Framework for Monitoring Patients with Alzheimer's and Other Dementias," 2019 International Conference on Systems, Signals and Image Processing (IWSSIP), Osijek, Croatia, 2019, pp. 175-180, doi: 10.1109/IWSSIP.2019.8787250 (Year: 2019).*
Isha Goel, "Design and Implementation of Android Based Wearable Smart Locator Band for People with Autism, Dementia, and Alzheimer".
Roy P. C. Kessels, "Landmark Recognition in Alzheimer's Dementia".
Matthew Stuart, "Google just showed off an incredible camera app that identifies real-world objects".
Google Keep, "https://leapfrogservices.com/4-top-location-based-reminder-apps-say-goodbye-forgetting".
Visual schedule Planner, "https://search.bridgingapps.org/apps/0f852d0a-224d-f9ca-fc4d-406355a5dd91".

* cited by examiner

METHOD, SYSTEM, AND DEVICE FOR PROVIDING ASSISTANCE TO PATIENTS WITH COMMUNICATION AND MEMORY IMPAIRMENT

TECHNICAL FIELD

Generally, the invention relates to devices for providing assistance to patients. More specifically, the invention relates to method, system, and device for providing assistance to patients with communication and memory impairment.

BACKGROUND

Typically, patients with communication and memory impairment (for example, an autistic kid or an Alzheimer's patient) face difficulty in communicating with people, identifying people, objects, and making a coherent communication. People suffering from similar other health issues may face similar difficulties. Such patients often forget recent events due to memory impairment or experience memory lapses at times and thus require constant assistance and support from a person, who may remind them of performing daily activities, like going to school, taking a bath, eating food, taking medicines, and the like. Such person providing assistance may either be a nurse trained to handle such patients or a family member. A person outside family or an untrained person may not be able to help these patients in case they require help and assistance. Thus, constant companionship and assistance may be required by such patients.

Today, various conventional systems and devices are available for providing assistance to such patients. However, some of these conventional devices are either not portable or are not feasible to be used at certain locations. Thus, either the device needs to be available at a given location or in case of infeasibility of the location to support the device, a person who can assist the patient may need to be present at that location. Further, some other conventional devices may only provide predefined sequential steps that are to be performed by a patient and may not be programmed to handle or manage any inconsistency in an activity performed by the patient.

There is therefore, a need for a method, system, and device that provides assistance to a patient by providing sequential steps associated with daily activities, and notifies the patient as well as a third person in case of any discrepancy in the patients activity, by continuously monitoring the patient.

SUMMARY OF INVENTION

In one embodiment, a method for providing assistance to patients with communication and memory impairment is disclosed. The method may include creating a database comprising a plurality of information elements structured as a dependency tree, based on a first set of information corresponding to a plurality of events associated with a patient. It should be noted that each of the plurality of information elements may be associated with at least one event of the plurality of events. The method may further include acquiring, in real-time, a second set of information associated with the patient. The method may further include matching the second set of information with each of the plurality of events in the database to identify at least one matching event and with at least one information element associated with the at least one matching event to identify a set of matching information elements. The method may further include comparing the second set of information with the set of matching information elements based on a predefined set of rules to identify at least one discrepancy. The method may further include prompting the patient to perform at least one predetermined action in response to identifying the at least one discrepancy.

In another embodiment, a method for providing assistance to patients with communication and memory impairment is disclosed. The method may include creating a database comprising a plurality of information elements structured as a dependency tree, based on a first set of information corresponding to a plurality of events associated with a patient. It should be noted that each of the plurality of information elements may be associated with at least one event of the plurality of events. The method may include acquiring, in real-time, a second set of information associated with the patient. The method may include rendering a plurality of context-based inquiry options to the patient, based on the second of information. The method may include receiving, from the patient, a selection of at least one context-based inquiry option from the plurality of context-based inquiry options. The method may include matching attributes of the at least one context-based inquiry option with each of the plurality of events in the database to identify at least one matching event and with at least one information element associated with the at least one matching event to identify a set of matching information elements. The method may include comparing the second set of information with the set of matching information elements based on a predefined set of rules to identify at least one discrepancy. The method may include prompting the patient to perform at least one predetermined action in response to identifying the at least one discrepancy.

In yet another embodiment, a device for providing assistance to patients with communication and memory impairment is disclosed. The device may include a processor and a memory communicatively coupled to the processor. The memory may store processor-executable instructions, which, on execution, may causes the processor to create, based on a first set of information corresponding to a plurality of events associated with a patient, a database comprising a plurality of information elements structured as a dependency tree. It should be noted that each of the plurality of information elements is associated with at least one event of the plurality of events. The processor-executable instructions, on execution, may further cause the processor to acquire, in real-time, a second set of information associated with the patient. The processor-executable instructions, on execution, may further cause the processor to match the second set of information with each of the plurality of events in the database to identify at least one matching event and with at least one information element associated with the at least one matching event to identify a set of matching information elements. The processor-executable instructions, on execution, may further cause the processor to compare the second set of information with the set of matching information elements based on a predefined set of rules to identify at least one discrepancy. The processor-executable instructions, on execution, may further cause the processor to prompt the patient to perform at least one predetermined action in response to identifying the at least one discrepancy.

It is to be understood that both the foregoing general description and the following detailed description are exemplary and explanatory only and are not restrictive of the invention, as claimed.

BRIEF DESCRIPTION OF THE DRAWINGS

The present application can be best understood by reference to the following description taken in conjunction with the accompanying drawing figures, in which like parts may be referred to by like numerals

DETAILED DESCRIPTION OF THE DRAWINGS

The following description is presented to enable a person of ordinary skill in the art to make and use the invention and is provided in the context of particular applications and their requirements. Various modifications to the embodiments will be readily apparent to those skilled in the art, and the generic principles defined herein may be applied to other embodiments and applications without departing from the spirit and scope of the invention. Moreover, in the following description, numerous details are set forth for the purpose of explanation. However, one of ordinary skill in the art will realize that the invention might be practiced without the use of these specific details. In other instances, well-known structures and devices are shown in block diagram form in order not to obscure the description of the invention with unnecessary detail. Thus, the invention is not intended to be limited to the embodiments shown, but is to be accorded the widest scope consistent with the principles and features disclosed herein.

While the invention is described in terms of particular examples and illustrative figures, those of ordinary skill in the art will recognize that the invention is not limited to the examples or figures described. Those skilled in the art will recognize that the operations of the various embodiments may be implemented using hardware, software, firmware, or combinations thereof, as appropriate. For example, some processes can be carried out using processors or other digital circuitry under the control of software, firmware, or hardwired logic. (The term "logic" herein refers to fixed hardware, programmable logic and/or an appropriate combination thereof, as would be recognized by one skilled in the art to carry out the recited functions.) Software and firmware can be stored on computer-readable storage media. Some other processes can be implemented using analog circuitry, as is well known to one of ordinary skill in the art. Additionally, memory or other storage, as well as communication components, may be employed in embodiments of the invention.

Figure 1:
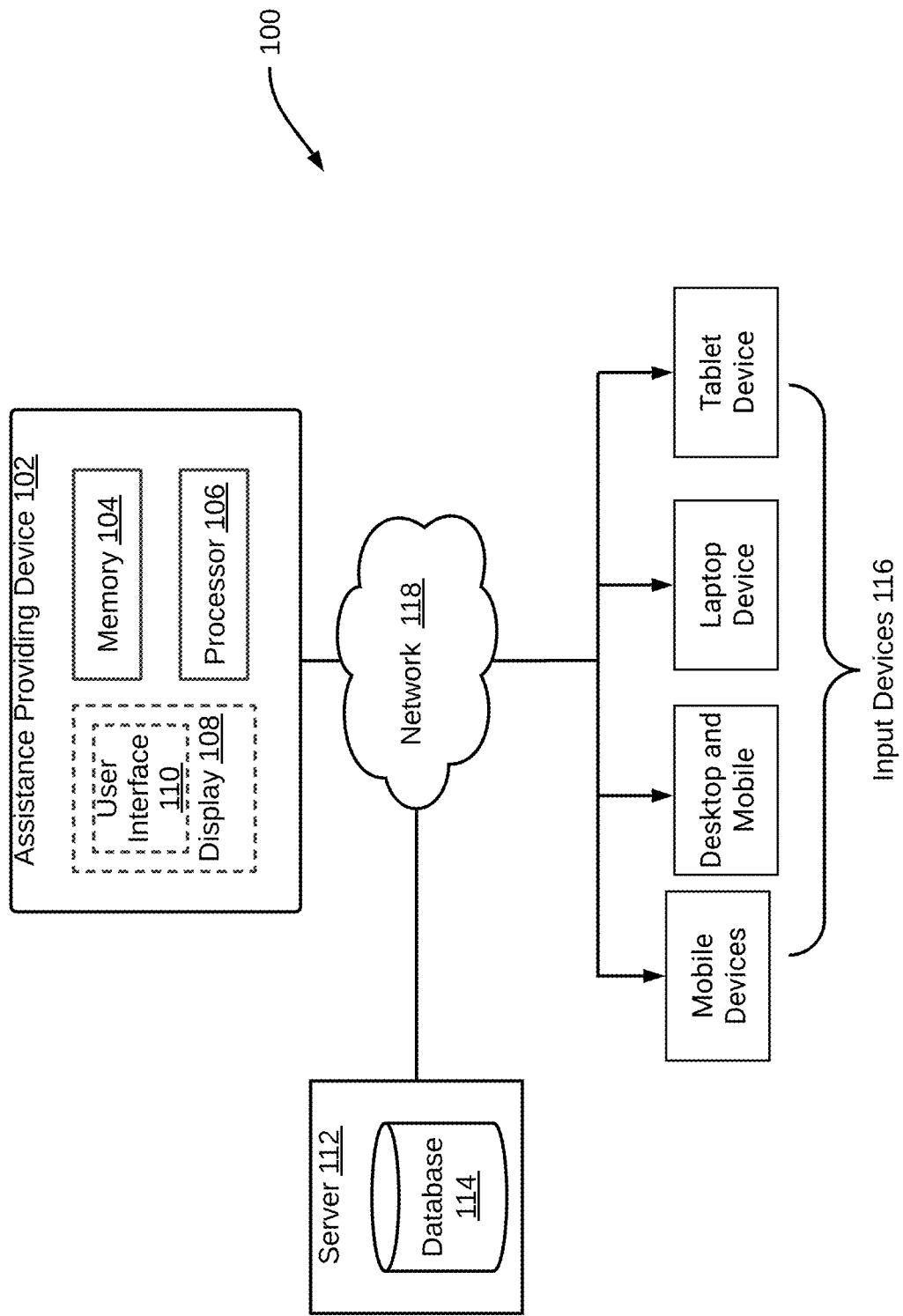
FIG. 1 is a block diagram illustrating a system for providing assistance to patients with communication and memory impairment, in accordance with an embodiment.

Referring now to FIG. 1, a block diagram of a system 100 for providing assistance to patients with communication and memory impairment is illustrated, in accordance with an embodiment. The system 100 may include an assistance providing device 102 that may prompt a patient to perform at least one predetermined action. By way of an example, the patient may include autistic kids, a person suffering from Alzheimer, and the like. In some embodiments, the assistance providing device 102 may gather a first set of information associated with a patient and may link the first set of information to create a database in which a plurality of information elements may be structured as a dependency tree. The first set of information may correspond to a plurality of events associated with the patient. Each of the plurality of information elements may be associated with at least one event of the plurality of events. A first subset of the first set of information may be dynamically captured via at least one of a plurality of sensors (not shown in FIG. 1). Additionally, a second subset of the first set of information may be received from at least one authorized person associated with the patient.

In another embodiment, a second set of information associated with the patient may be gathered by the assistance providing device 102, in real-time. Thereafter, based on the database and second set of information, the assistance providing device 102 may provide assistance to the respective patient.

Additionally, in some embodiments, the assistance providing device 102 may display a plurality of context-based inquiry options to the patient. The patient may select at least one context-based inquiry option from the plurality of context-based inquiry option. Thus, assistance providing device 102 may provide assistance to the patient based on the selected context-based enquiry option and the database. This is further explained in detail in conjunction with FIG. 2 to FIG. 7.

Examples of the assistance providing device 102 may include, but are not limited to a smartphone, a mobile phone, a smart watch, smart-band, a smart wearable, or the like. The assistance providing device 102 may include a memory 104, a processor 106, and a display 108. The display 108 may further include a user interface 110. A user, the patient or an administrator may interact with the assistance providing device 102 and vice versa through the display 108. By way of an example, the display 108 may be used to display results of analysis performed by the assistance providing device 102, to the user. By way of another example, the user interface 110 may be used by the user to provide inputs to the assistance providing device 102. Thus, for example, in some embodiments, the assistance providing device 102 may ingest information such as a video data, an audio data, and an image data associated with the patient and one or more selected options provided by the user/patient/administrator via the user interface 110. Further, for example, in some embodiments, the assistance providing device 102 may render results to the user/administrator via the user interface 110. In some embodiments, the user/administrator may provide inputs to the assistance providing device 102 via the user interface 110.

The memory 104 may store instructions that, when executed by the processors 106, may cause the processors 106 to provide assistance to the patients, in accordance with some embodiments. As will be described in greater detail in conjunction with FIG. 2 to FIG. 10, in order to provide assistance to patients, the processor 106 in conjunction with the memory 104 may perform various functions including creating a database, acquiring real time information, identifying matching information, identifying discrepancies, and prompting the patient to perform at least one predetermined action.

The memory 104 may also store various data (e.g. a video data, an audio data, and an image data associated with the patient, a plurality of events, an image of an object, details associated with the object, time details, relation with a person, details of a person, an audio sound, a location, a name of the location, a video, and a phone number etc.) that may be captured, processed, and/or required by the assistance providing device 102. The memory 104 may be a non-volatile memory (e.g., flash memory, Read Only Memory (ROM), Programmable ROM (PROM), Erasable PROM (EPROM), Electrically EPROM (EEPROM) memory, etc.) or a volatile memory (e.g., Dynamic Random Access Memory (DRAM), Static Random-Access memory (SRAM), etc.)

Further, the assistance providing device 102 may interact with a server 112 or input devices 116 via a communication network 118 for sending and receiving various data. The communication network 118, for example, may be any wired or wireless communication network and the examples may include, but may be not limited to, the Internet, Wireless Local Area Network (WLAN), Wi-Fi, Long Term Evolution (LTE), Worldwide Interoperability for Microwave Access (WiMAX), and General Packet Radio Service (GPRS).

By way of an example, in some embodiments, the assistance providing device 102 may receive the first set of information from the server 112 or the input devices 116 and the second set of information may be captured directly by the assistance providing device 102. The server 112 may further include a database 114, which may store information related to a patient, such as, a video data, an audio data, and an image data associated with the patient. Further, the input devices 116 may include, but may not be limited to a desktop, a laptop, a notebook, a netbook, a tablet, a smartphone, a remote server, a mobile phone, or another computing system/device. In an embodiment, one or more of the input devices 116 may be used to perform initial configuration of the assistance providing device 102. Additionally, the assistance providing device 102 may validate user access over one of these input devices 116.

Figure 2:
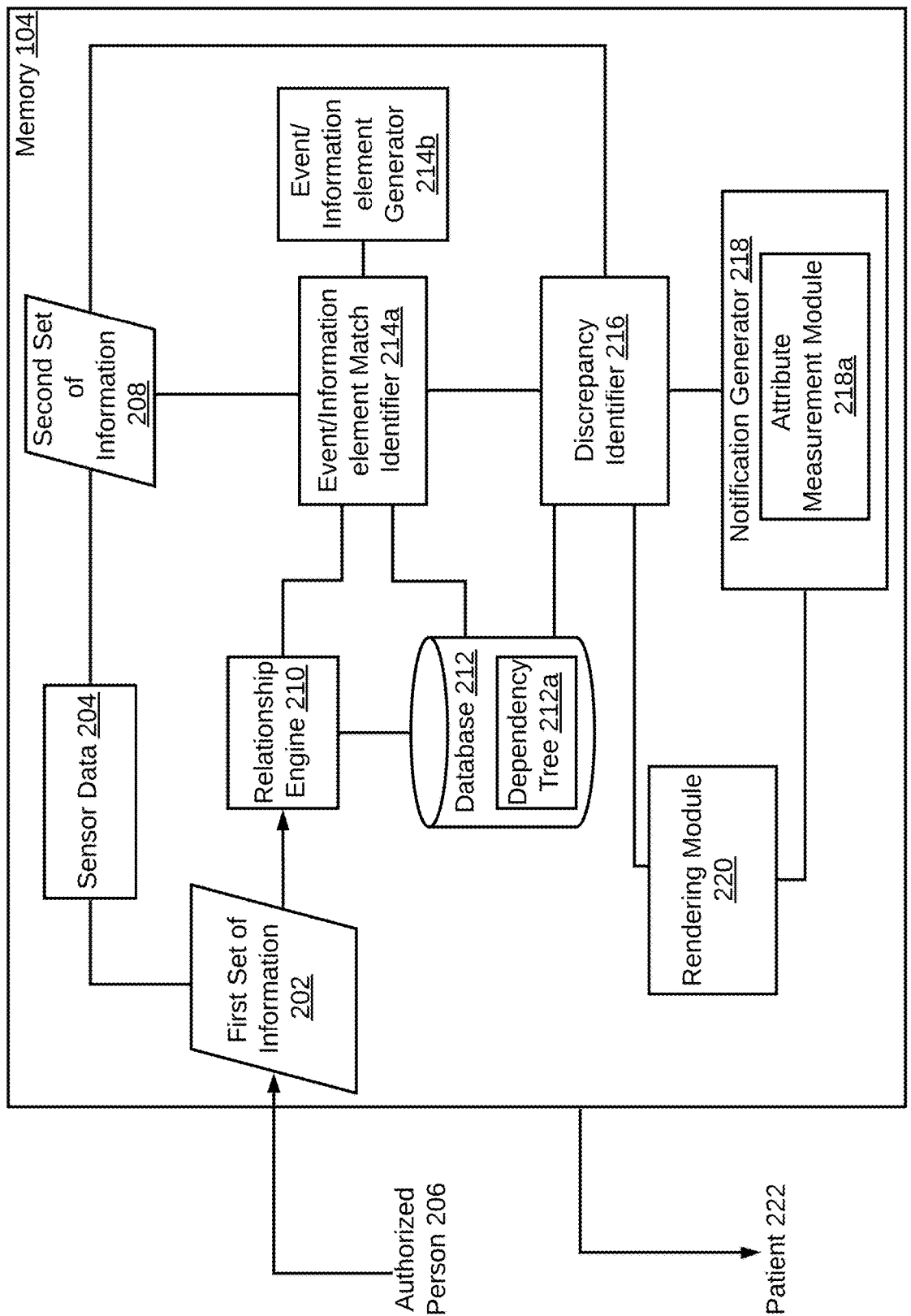
FIG. 2 is a functional block diagram of various modules within a memory of an assistance providing device configured to provide assistance to patients with communication and memory impairment, in accordance with an embodiment.

Referring now to FIG. 2, a block diagram of various modules within the memory 104 of the assistance providing device 102 configured to provide assistance to patients with communication and memory impairment is illustrated, in accordance with an embodiment. Initially, the assistance providing device 102 may collect a first set of information 202 corresponding to a plurality of events associated with a patient. The plurality of events may include one or more of an activity associated with the patient, an un-expected action performed by the patient, a voluntary or involuntary action performed by the patient, absence of an action performed by the patient within a predefined time period, or an action performed by a person in vicinity of the patient. The first set of information 202 may further include two subsets, i.e. a first subset of the first set of information and a second subset of the first set of information.

The first subset of the first set of information 202 may be extracted from sensor data 204 gathered by a plurality of sensors (not shown in FIG. 1) within the assistance providing device 102, and the second subset of the first set of information 202 may be provided by an authorized person 206. The plurality of sensors may also be configured to acquire a second set of information 208 upon requirement or iteratively after every predefined time interval. Examples of the plurality of sensors may include, but are not limited to a camera, a motion sensor, a proximity sensor, a microphone, a gyroscope, an accelerometer, a proximity sensor, an Infra-Red (IR) sensor, a light sensor, an ultrasonic sensor, a pulse sensor, a pulse oximeter, a Radio Frequency Identification (RFID) sensor, a Near-field Communication (NFC) sensor, or a temperature sensor. By way of an example, the camera may be used to capture a video data, and an image data associated with the patient, while the microphone may be used to capture voice of the patient or that of the people near the patient. By way of another example, the gyroscope or the accelerometer may be used to determine whether the patient has had a fall or an accident.

In order to provide assistance to the patients with communication and memory impairment, the memory 104 may include a relationship engine 210, a database 212, an event/Information element match identifier 214a, an event/Information element generator 214b, a discrepancy identifier 216, a notification generator 218, and a rendering module 220. Further, the first set of information 202 may be provided to the relationship engine 210 that may create the database 212 based on the first set of information 202. Further, the database 212 may include a dependency tree 212a. The dependency tree 212a may be a combination of a plurality of information elements that are structured or connected in the form of a dependency tree. Each of the plurality of information element may represent a node of the dependency tree, which is explained in greater detail in conjunction with the FIG. 9.

With regards to the plurality of information elements, at least one of an image of an object, details associated with the object, time details, relation with a person, details of a person, an audio sound, a location, a name of the location, a video, and a phone number may form the dependency tree 212a. It may be noted that each of the plurality of information elements is associated with at least one event of the plurality of events.

Further, the event/information element match identifier 214a may be communicatively coupled to the relationship engine 210 and the database 212. The event/information element match identifier 214a may be configured to match the second set of information 208 with each of the plurality of events in the database 212 to identify at least one matching event. In some embodiments, the event/information element match identifier 214a may match the second set of information 208 with at least one information element associated with the at least one matching event to identify a set of matching information elements. It should be noted that the plurality of sensors may acquire the second set of information 208 associated with the patient and may then transmit the second set of information 208 to the event/information element match identifier 214a. The event/information element match identifier 214a may share the set of matching information elements with the discrepancy identifier 216. Also, when at least one of a matching event or a matching information element is not identified, the event/information element match identifier 214a may transmit a signal to the event/information element generator 214b.

The event/information element generator 214b is communicatively coupled to the event/information element match identifier 21a4. The event/information element generator 214b may be configured to generate a new event or a new information element. When at least one of a matching event and a matching information element is absent, the event/information element generator 214b may generate the new event or a new information element. In some embodiments, the generated new event or the new information element may be added to the dependency tree 212a of the database 212 directly or via the relationship engine 210. In other words, the database 212 may be updated with the new information. In order to update the database 212, at least one of a new event and new dependency relationships may be created amongst the second set of information 208 and with the new event. The information of updated database 212 may be further validated by the authorized person 206. The authorized person 206 may have the right to amend information in the database 212 based on the current situation.

The discrepancy identifier 216 may be operatively connected to the database 212, and the event/information element match identifier 214a. The discrepancy identifier 216 may be configured to receive the set of matching information elements from the event/information element match identifier 214a. Additionally, the discrepancy identifier 216 may extract the second set of information 20 from the sensor data 204. A comparison between the set of matching information elements and the second set of information 208 may be performed by the discrepancy identifier 216. Based on the comparison, the discrepancy identifier 216 may identify the at least one discrepancy. A discrepancy, for example, may include deviation from a predefined series of steps or introduction of a new event, which is not already included in the database 212. The discrepancy identifier 216 may transmit a signal to the communicatively coupled notification generator 218 upon identification of the at least one discrepancy.

The notification generator 218 may be configured to generate a notification. Upon identification of any discrepancy by the discrepancy identifier 216, the notification generator 218 may generate the notification. The notification may be rendered to the patient via the rendering module 220 and/or may be sent to one or more authorized persons. The notification generator 218 may include an attribute measurement module 218a. The attribute measurement module 218a may determine or measure patient attributes, which may include, but are not limited to respiratory rate, heart rate, blood pressure, body gesture, and galvanic skin response of the patient. One or more of the measured patient attributes may be included in the notification generated by the notification generator 218. Additionally, in some embodiments, discrepancy may be identified based on any anomaly in the measured attributes and the notification may subsequently be generated. The anomaly may be generated in various situations, for example, when the patient is panicking, is running, is under stress, gets hiccups, or sighs. The discrepancy identifier 216 may also help in identifying such a situation and the notification may include details related to the situation so identified.

The assistance providing device 102 may automatically provide some warnings (by way of the notification), in case an activity that is not safe or not as per pre-defined steps is detected by the discrepancy identifier 216. By way of an example, a patient may step out from a pool and may directly go into a street without entering into a dressing-room and changing into suitable clothing. This will prompt the notification generator 218 to generate a notification to the patient as well as to an authorized person. Similarly, by way of another example, a patient may start walking on the road instead of waiting for a bus in a waiting room or may access a place where the patient is not supposed to be present at a given time based on a predefined agenda. In that case, notifications (warnings or alerts) may be generated by the notification generator 218.

In an embodiment, predefined rules that lead to generation of a notification may be modified in real-time by an authorized person. By way of an example, an authorized person, say Robert, usually goes to pick up a patient, say John, at a swimming pool. However, Robert may not be able to pick John on a certain day. In such a case, as Robert is an authorized person and has rights to override predefined information and the predefined rules fed into the assistance providing device 102, Robert may make some changes in the predefined rules and/or the predefined information. The changes, for example, may include appointing another person, say Bob, in place of Robert to pick up John. Thus, absence of Robert to pick up John may not lead to generation of a warning to other authorized persons. Additionally, John may also be informed regarding the change by way of a notification. The notification, for example, may include Bob's name and his picture. In an embodiment, the notification module 218 may notify other authorized persons of such changes made by Robert. Other authorized persons, for example, may include John's grandparents, John's parents, brother, and/or sister. In this case, either one or all of the other authorized persons may be required to confirm the change. In other words, any change made by an authorized person may be required to be validated by one or more other authorized persons. Such validation process and requirement may be set when the assistance providing device 102 is configured.

In addition to rendering notifications or warnings to a patient, the rendering module 220, may render a plurality of sequential steps associated with a particular event to the patient 222. In some embodiments, the rendering module 220 may provide a plurality of context-based inquiry options to the patient 222 and the patient 222 may select at least one of the plurality of context-based inquiry options. The rendering to the patient 222 may be performed by the rendering module 220 as at least one of a pop up message, an audio message, a video message or a text message.

The assistance providing device 102 may work in a learning phase and an activation phase. In the learning phase, the assistance providing device 102 may gather information by identifying objects associated with certain events, their locations and the involved persons. In some embodiments, the assistance providing device 102 may automatically perform identification via Global Positioning System (GPS), RFID, Bluetooth, electronic calendar access, pictures, videos, etc. In some other embodiments, to aid configuration of the assistance providing device 102, identification using tagged pictures, tagged voices, place information, information related to people (such as, their names, phone numbers, addresses, time, etc) may be performed manually.

It should be noted that the gathered information may be associated with an activity, a place, or a person. The learning phase never stops, as the database 212 is continuously updated with new information either automatically or manually. By way of an example, a new friend or a new place or a new GPS location is identified along with a certain activity and this is required to be added in the database 212 as information elements due to permanence for a certain amount of time. The identified new place may be added to a list of frequented places and information of all the objects associated to that place may be gathered by capturing pictures from outside, inside, or may be downloaded from internet for that location, name of the event/place, surrounding sounds (for example, birds in the park or splash in the swimming pool, gym instructor voice and the like). In an embodiment, the new gathered information may also be manually examined and validated by an authorized person (such as, parents of the patient 222), before getting them operative. Additionally, the authorized person may manually provide for some additional new information, for example, friends' names, phone numbers, Bluetooth identifiers, pictures, voices, and may integrate or correct the existing ones.

In the activation phase, all the available information in the database 212 may be utilized and inquired either manually or automatically. In the activation phase, the second set of information 208 may be captured using the plurality of sensors. By way of an example, a camera of the assistance providing device 102 may capture an image and may then match it with the information elements of the database 212. The matching information may be extracted and the information related to the image, such as, description, people in the image, or sounds may be rendered by the assistance providing device 102. Example of information may include, but are not limited to this is your school, this is your classroom, these are your preferred class-mates, she is your teacher, he is your bus driver, and the like. As explained before, in some embodiments, the patient 222 may manually trigger the assistance providing device 102, by pushing an inquiry button or selecting a context-based inquiry option. The output generated by the assistance providing device 102 may be graphical, haptic, or vocal.

Moreover, the assistance providing device 102 may also generate the output based on a detected voice. For example, when a bus diver says, "Come here John!," the assistance providing device 102 may recognize the driver's voice and may subsequently display a photo of the bus, the driver's photo, home address, and a picture of house, on the display 108 of the assistance providing device 102. Further, the information elements may be recursively extracted (automatically or manually), based on provided input, time-frame, and current location of the assistance providing device 102 (in other words, location of the patient 222). Additionally, the assistance providing device 102 may also provide a time-frame to place information for a specific object or event, when its presence is detected (for example, on Monday or 20 years ago). The presence of the event or object may be detected by means of at least one of an RFID sensor, an NFC sensor, a Bluetooth sensor, or a barcode module.

It should be noted that the assistance providing device 102 may be implemented in programmable hardware devices such as programmable gate arrays, programmable array logic, programmable logic devices, or the like. Alternatively, the assistance providing device 102 may be implemented in software for execution by various types of processors. An identified engine/module of executable code may, for instance, include one or more physical or logical blocks of computer instructions which may, for instance, be organized as an object, module, procedure, function, or other construct. Nevertheless, the executables of an identified engine/module need not be physically located together but may include disparate instructions stored in different locations which, when joined logically together, comprise the identified engine/module and achieve the stated purpose of the identified engine/module. Indeed, an engine or a module of executable code may be a single instruction, or many instructions, and may even be distributed over several different code segments, among different applications, and across several memory devices.

As will be appreciated by one skilled in the art, a variety of processes may be employed to provide assistance to the patients with communication and memory impairment. For example, the exemplary system 100 and the assistance providing device 102 may provide assistance to patients with communication and memory impairment, by the process discussed herein. In particular, as will be appreciated by those of ordinary skill in the art, control logic and/or automated routines for performing the techniques and steps described herein may be implemented by the system 100 and the assistance providing device 102 either by hardware, software, or combinations of hardware and software. For example, suitable code may be accessed and executed by the processor 106 in the assistance providing device 102 to perform some or all of the techniques described herein. Similarly, application specific integrated circuits (ASICs) configured to perform some or all the processes described herein may be included in the processor 106 in the assistance providing device 102.

Figure 3:
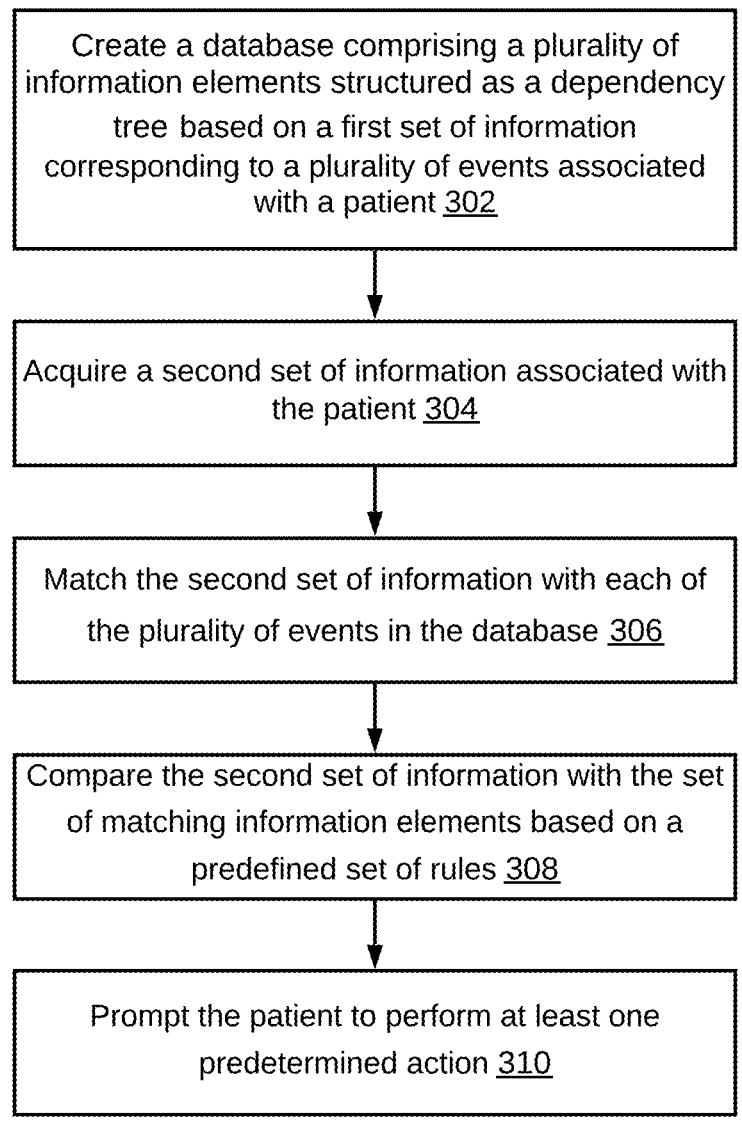
FIG. 3 is a flowchart of a method for providing assistance to patients with communication and memory impairment, in accordance with an embodiment.

Referring now to FIG. 3, a flowchart of a method for providing assistance to patients with communication and memory impairment is illustrated, in accordance with an embodiment. Each step of the method may be executed by the assistance providing device 102. At step 302, a database (for example, the database 212) may be created by a relationship engine (for example, the relationship engine 210) in the assistance providing device 102. It should be noted that the database may be created based on a first set of information corresponding to a plurality of events associated with a patient.

The database may include a plurality of information elements that are structured as a dependency tree. In other words, the plurality of information elements together may form a tree like structure. It should also be noted that each of the plurality of information elements may be associated with at least one event of the plurality of events. Further, the plurality of events may include at least one of an activity associated with the patient, an un-expected action performed by the patient, a voluntary or involuntary action performed by the patient, absence of an action performed by the patient within a predefined time period, or an action performed by a person in vicinity of the patient. The plurality of information elements in the database may include at least one of an image of an object, details associated with the object, time details, relation with a person, details of a person, an audio sound, a location, a name of the location, a video, and a phone number.

At step 304, a second set of information associated with the patient may be acquired in real-time. A plurality of sensors may be used to acquire the second set of information. It may be noted that the first set of information and the second set of information may include a video data, an audio data, and an image data associated with the patient. It may be further noted that the plurality of sensors comprises at least one of a camera, a sound sensor, a proximity sensor, an IR sensor, a light sensor, an ultrasonic sensor, a temperature sensor, and pulse meter. This has already been explained in detail in conjunction with FIG. 2.

At step 306, the second set of information may be matched with each of the plurality of events in the database and with at least one information element associated with the at least one matching event. In some embodiments, matching is performed with each of the plurality of events in the database in order to identify at least one matching event. In some other embodiments, the matching is performed with at least one information element associated with the at least one matching event to identify a set of matching information elements. This has already been explained in detail in conjunction with FIG. 2.

At step 308, the second set of information may be compared with the set of matching information elements. It may be noted that the comparing may be performed based on a predefined set of rules to identify at least one discrepancy. In an embodiment, discrepancy may also correspond to actions performed by the patient that may get the patient involved with a dangerous situation. By way of an example, a dangerous situation may include the patient may trying to enter a closed door that cannot be used due to ongoing construction work. By way of another example, the patient may attempting to enter a swimming pool with the coat and the suits or may enter a place where there are visible dangers such as flames or people running out. Other example of such dangerous situations may include using a wrong routing path or leaving open the water hose or a gas pipeline. At step 310, the patient may be prompted to perform at least one predetermined action in response to identifying the at least one discrepancy. In continuation of the example above, once a discrepancy in the form of a dangerous situation is identified, the patient may be notified that the action being performed by the patient may have dangerous consequences for the patient or for others.

Figure 4:
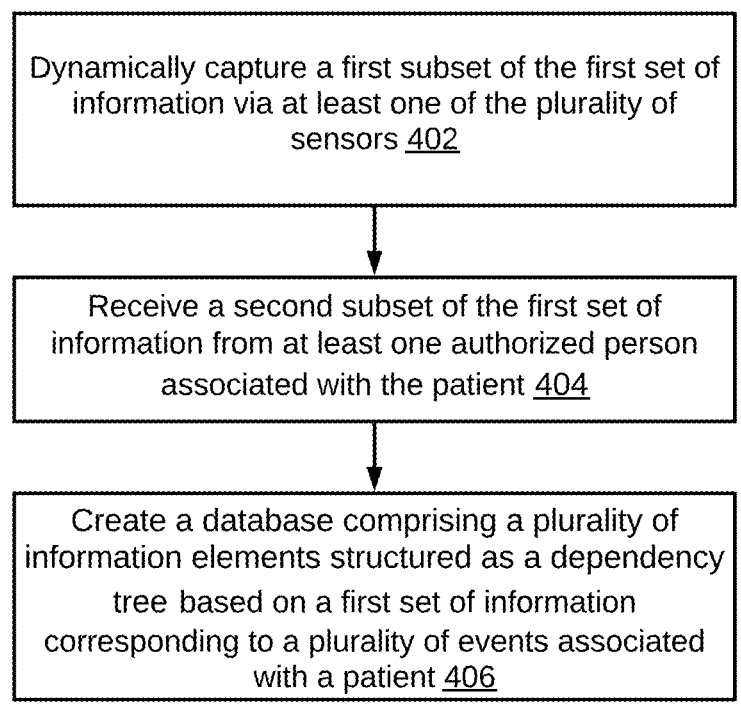
FIG. 4 is a flowchart of a method for creating a database that includes a plurality of information elements, in accordance with an embodiment.

Referring now to FIG. 4, a flowchart of a method for creating the database 212 that includes a plurality of information elements is illustrated, in accordance with an embodiment. At step 402, a first subset of the first set of information may be captured dynamically. It may be noted that the plurality of sensors may be used to capture the first subset of the first set of information. The plurality of sensors may include at least one of a camera, a sound sensor, a proximity sensor, an IR sensor, a light sensor, an ultrasonic sensor, a temperature sensor, and pulse meter. At step 404, a second subset of the first set of information may be received. It may be noted that at least one authorized person (for example, the authorized person 206) associated with the patient may provide the second subset of the first set of information.

At step 406, the database 212 may be created by the relationship engine of the assistance providing device 102. Further, the database 212 may include a plurality of information elements structured as a dependency tree. It may be noted that the database 212 may be created based on both the subsets of the first set of information that may correspond to a plurality of events associated with a patient. It may further be noted that each of the plurality of information elements is associated with at least one event of the plurality of events.

Figure 5:
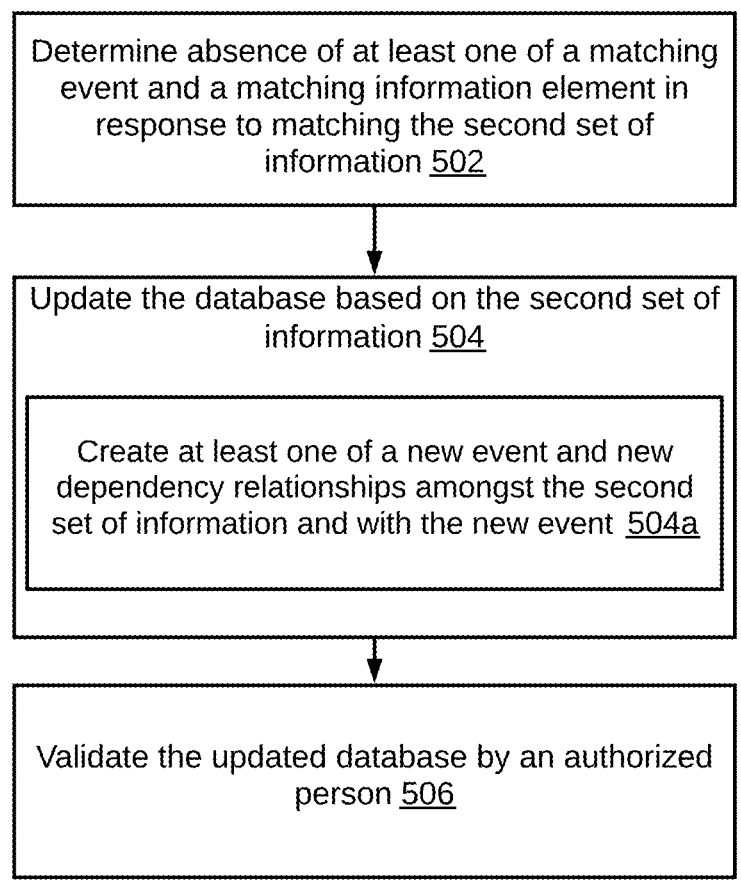
FIG. 5 is a flowchart of a method for updating a database that includes a plurality of information elements, in accordance with an embodiment.

Referring now to FIG. 5, a flowchart of a method for updating the database 212 that includes a plurality of information elements is illustrated, in accordance with an embodiment. Referring back to step 306 of FIG. 3, in response to matching the second set of information, absence of at least one of a matching event and a matching information element may be determined at step 502. Further, at step 504, the database 212 may be updated by a relationship engine 210 based on the second set of information. In some embodiments, at step 504a, at least one of a new event and new dependency relationships may be created amongst the second set of information and with the new event in order to update the database 212. At step 506, the updated database 212 may be validated by an authorized person. It may be noted that the authorized person may have the rights to modify information in the database 212.

Figure 6:
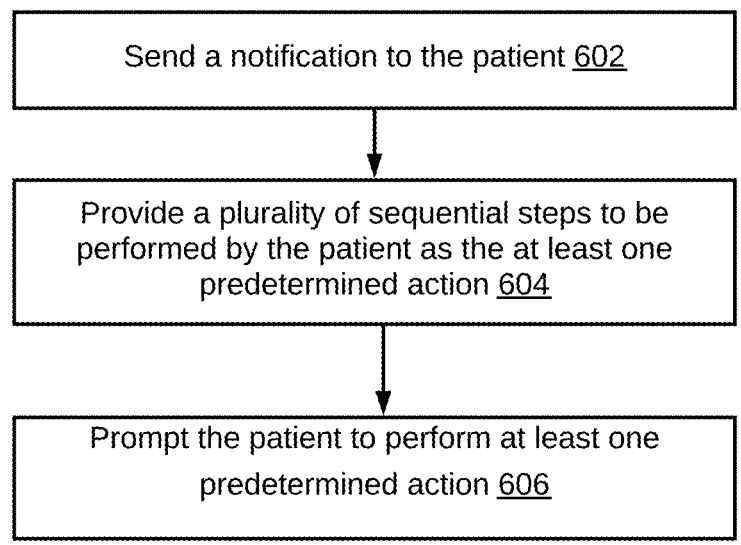
FIG. 6 is a flowchart of a method for prompting a patient to perform at least one predetermined action, in accordance with an embodiment.

Referring now to FIG. 6, a flowchart of a method for prompting a patient to perform at least one predetermined action is illustrated, in accordance with an embodiment. The patient may be prompted to perform the at least one predetermined action in response to identifying at least one discrepancy in response to comparing a second set of information with a set of matching information elements based on a predefined set of rules. This has already been explained in detail in step 310 of FIG. 3. At step 602, a notification may be sent to the patient in response to identifying the at least one discrepancy. At step 604, a plurality of sequential steps may be provided to the patient as the at least one predetermined action. At step 606, the patient may be prompted to perform the plurality of sequential steps. By way of an example, a patient may step out from a pool and may directly go into a street without entering into a dressing-room and changing into suitable clothing. This will be identified as a discrepancy and will prompt the notification generator 218 to generate a notification to the patient. The notification may include instructions for the patient, which may instruct the patient to go back into the dressing-room and to then change into suitable clothing.

Figure 7:
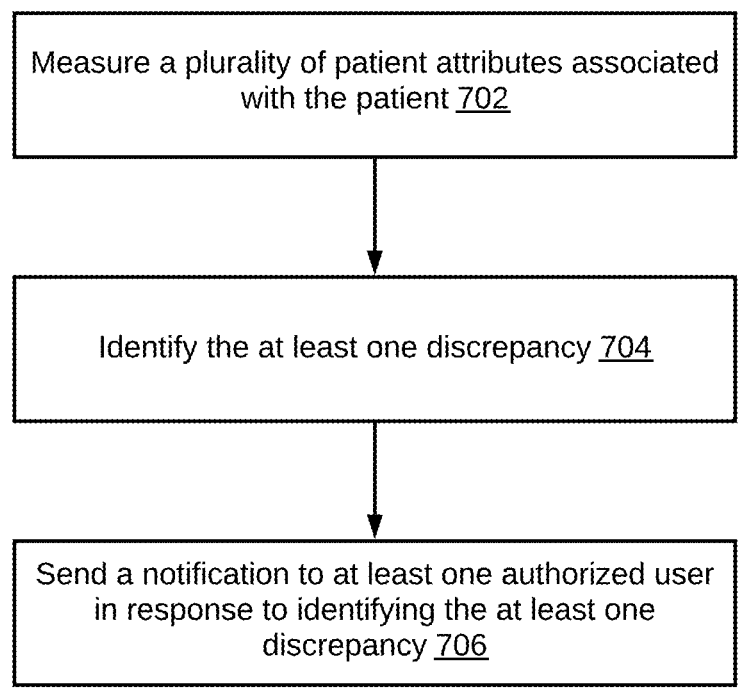
FIG. 7 is a flowchart of a method for sending a notification to an authorized person upon identification of any discrepancy associated with a patient, in accordance with an embodiment.

Referring now to FIG. 7, a flowchart of a method for sending a notification to an authorized person upon identification of any discrepancy is illustrated, in accordance with an embodiment. At step 702, a plurality of patient attributes may be measured. By way of an example, the patient attributes, may include but are not limited to respiratory rate, heart rate, blood pressure, body gesture, and galvanic skin response of the patient. Thereafter, at step 704, at least one discrepancy may be identified based on comparison of the plurality of patient attributes with associated predefined range or values. By way of an example, a discrepancy may correspond to deviation in values of the patient's attributes from their nominal values or range, an un-expected action performed by the patient, a voluntary or involuntary action performed by the patient, and the like. At step 706, a notification may be sent to the at least one authorized user in response to identifying the at least one discrepancy. This has already been explained in detail in conjunction with FIG. 2.

Figure 8:
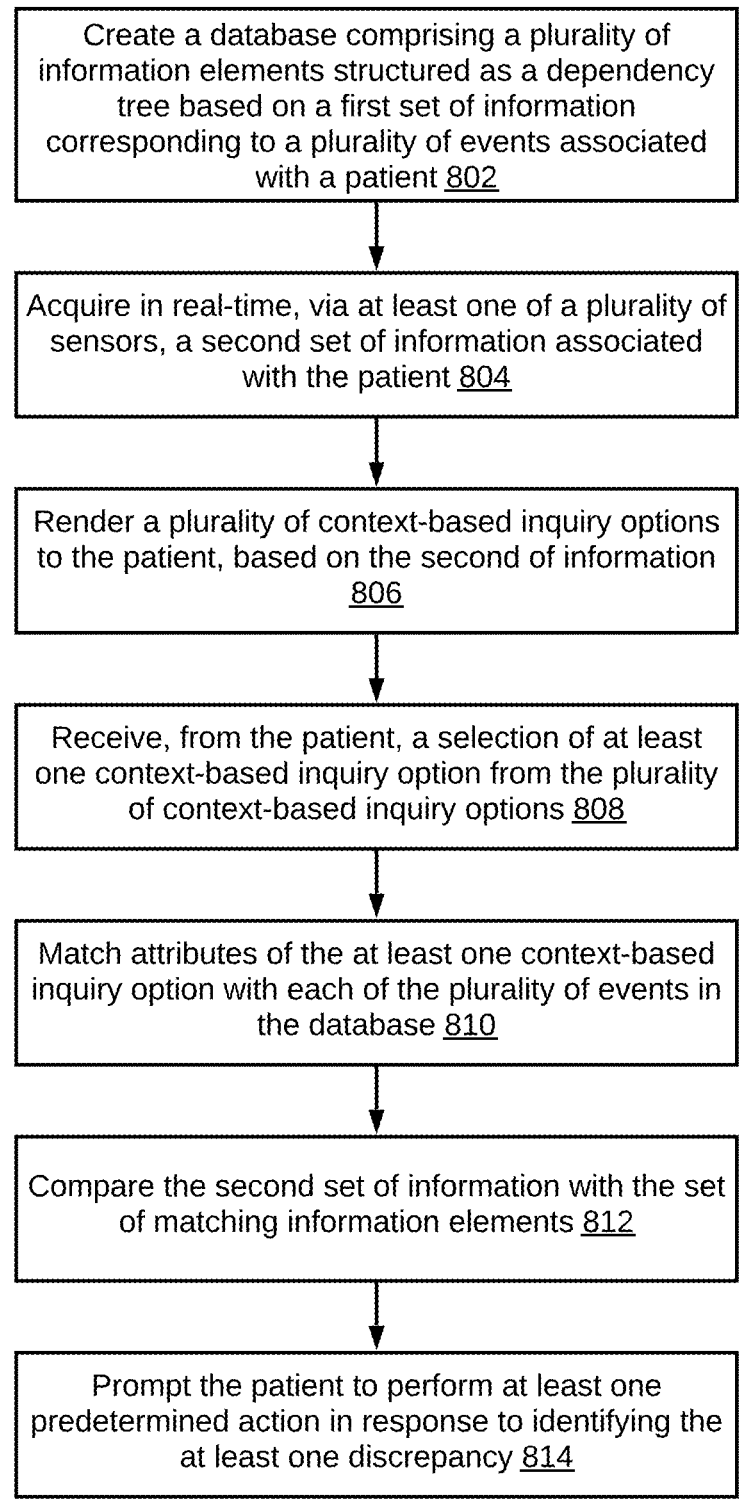
FIG. 8 is a flowchart of a method for providing assistance to patients with communication and memory impairment, in accordance with another embodiment.

Referring now to FIG. 8, a flowchart of a method for providing assistance to patients with communication and memory impairment is depicted via a flowchart, in accordance with another embodiment. At step 802, a database (for example, the database 212) may be created by a relationship engine of the assistance providing device 102. The database may be created based on a first set of information corresponding to a plurality of events associated with a patient. The plurality of events may include at least one of an activity associated with the patient, an un-expected action performed by the patient, a voluntary or involuntary action performed by the patient, absence of an action performed by the patient within a predefined time period, or an action performed by a person in vicinity of the patient. This has already been explained in detail in conjunction with FIG. 2 and FIG. 3.

Further, in some embodiments, a dependency tree may be generated to create the database. The dependency tree may include a plurality of information elements and dependency amongst each of the plurality of information elements and with at least one of the plurality of events. The plurality of information elements in the database may include at least one of an image of an object, details associated with the object, time details, relation with a person, details of a person, an audio sound, a location, a name of the location, a video, and a phone number. This has already been explained in detail in conjunction with FIG. 2 and FIG. 3.

At step 804, a second set of information associated with the patient may be acquired in real-time. A plurality of sensor may be employed to acquire the second set of information. Further, the plurality of sensors may include at least one of a camera, a sound sensor, a proximity sensor, an Infra-Red (IR) sensor, a light sensor, an ultrasonic sensor, a temperature sensor, and pulse meter. In some embodiments, the first set of information and the second set of information may include a video data, an audio data, and an image data associated with the patient At step 806, a plurality of context-based inquiry options may be rendered to the patient, based on the second set of information. At step 808, a selection of at least one context-based inquiry option from the plurality of context-based inquiry options may be received from the patient. At step 810, attributes of the at least one context-based inquiry option may be matched with each of the plurality of events in the database and with at least one information element associated with the at least one matching event. It should be noted that at least one matching event may be identified when attributes of the at least one context-based inquiry option are matched with each of the plurality of events in the database. Additionally, a set of matching information elements may be identified when attributes of the at least one context-based inquiry option are matched with the at least one matching event.

At step 812, the second set of information may be compared with the set of matching information elements. Further, a predefined set of rules may be utilized to identify at least one discrepancy based on the comparison. At step 814, the patient may be prompted to perform at least one predetermined action in response to identifying the at least one discrepancy. This has already been explained in detail in conjunction with FIG. 2 and FIG. 3.

Figure 9:
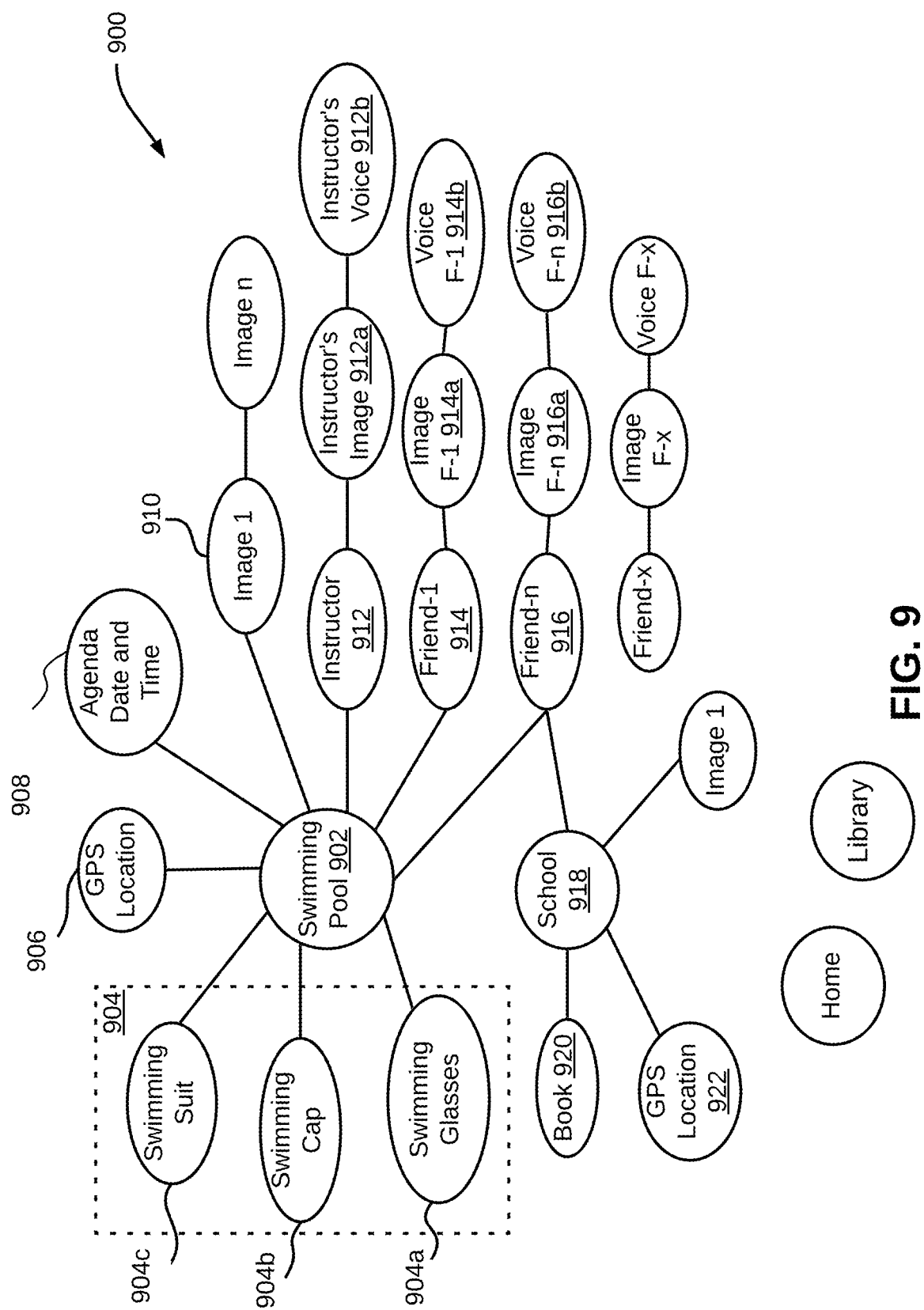
FIG. 9 illustrates a database structured as a dependency tree, in accordance with an exemplary embodiment.

Referring now to FIG. 9, a database 900 structured as a dependency tree is illustrated, in accordance with an exemplary embodiment. As the database 900 is structured as a dependency tree, the database 900 may include a plurality of nodes 902, 904, 906, 908, 910, 912, 914, 916, 918, and the like. The node 902 represents a swimming pool, which is connected to various nodes including different information elements associated with a user/patient and the swimming pool. Similar to the node 902, the database 900 may include some other nodes for different places, such as a node 918 for school. In the FIG. 9, it is clearly seen that the node 916 that includes information of friend 'n' is common for both the places, i.e., for the school (the node 918) and the swimming pool (the node 902). In other words, some information may be applied based on consistency with other parameters. For example, a friend may be tagged to school only, while another may be tagged to school as well as swimming pool. Further, a selection may be done based on the current GPS position of a patient.

In some embodiments, the database 900 may be created based on relations, such that, information may be organized with a key composed of columns, such as, name, date, time, topic, and other two possible event classifications/identifications. By way of an example, Riccardo, 10 Aug. 2018, 05:00 PM, swimming pool, and then all the associated event information. In this way, information (like, place information), images, music, voices (for example, animal cries, human voices) and any other related information may be fetched, aggregated, and organized in the database 900 to produce a value for the user/patient. Thus, information elements may be extracted by using one or more of the keys depending upon need.

In some other embodiments, the information may be organized defining dependencies among the information elements, thereby forming a dependency tree. The dependency tree may be used to extract the information elements according to a certain criterion. In an instruction phase, the system (such as, the system 100) may be instrumented by registering voices, capturing pictures of environment, automatically or manually inputting data inside the database 900, and so on. The information elements may be released when needed according to a dependency workflow.

Figure 10:
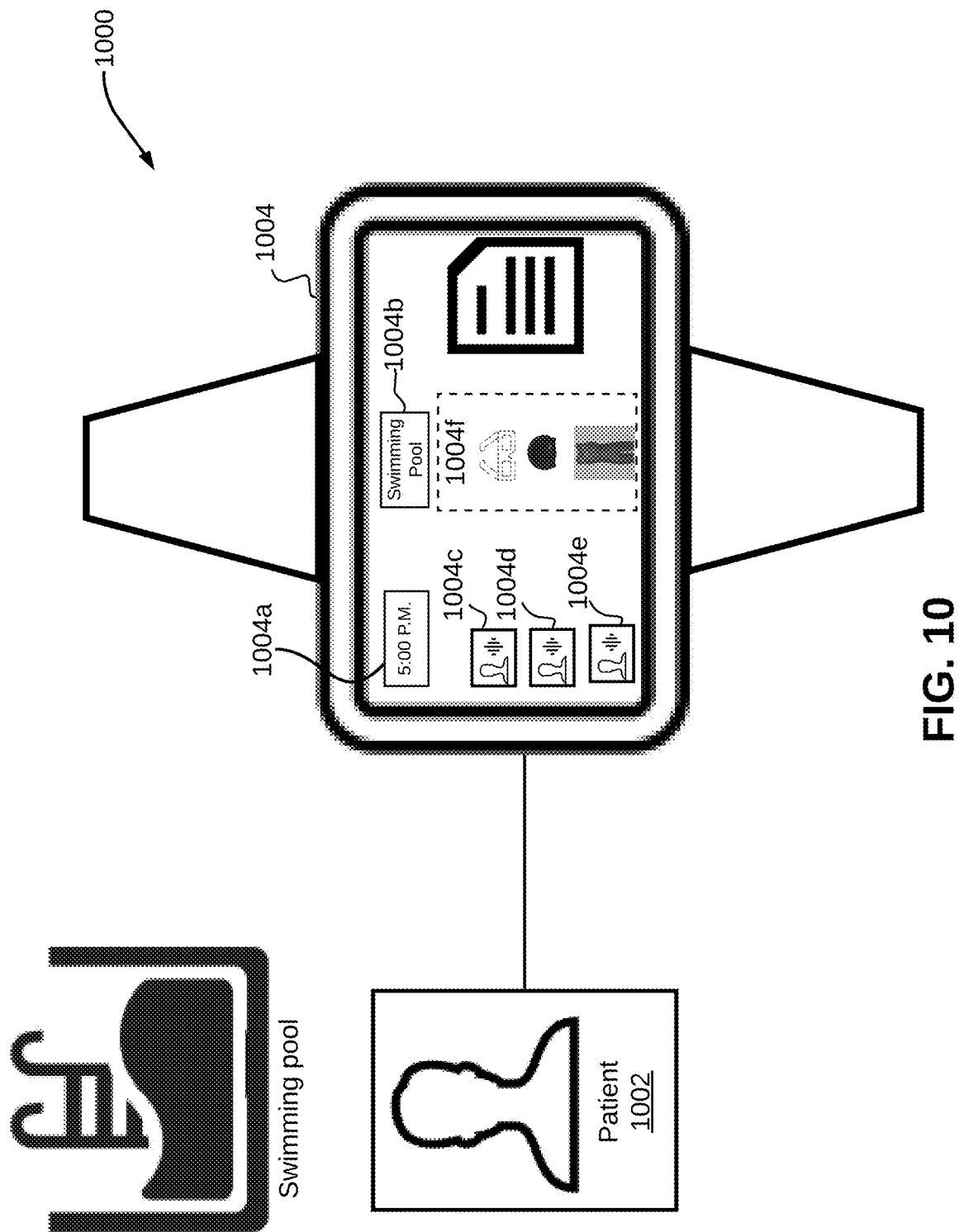
FIG. 10 illustrates a scenario depicting assistance being provided to a patient with communication and memory impairment through a smart watch that acts as an assistance providing device, in accordance with an exemplary embodiment. is illustrated

Referring now to FIG. 10, a scenario 1000 depicting providing assistance to a patient 1002 with communication and memory impairment through a smart watch 1004 (as the assistance providing device 102) is illustrated, in accordance with an exemplary embodiment. The patient 1002 wears the smart watch 1004 that is programmed and configured as the assistance providing device 102. Consider a situation, where the patient 1002 comes at a swimming pool every Monday, for a time duration between 5:00 PM to 6:00 PM. However, due to memory impairment the patient 1002 may forget the schedule, may perform steps that the patient 1002 is not supposed to perform, or may encounter events that the patient 1002 is not prepared to handle. Therefore, the patient 1002 always wears the smart watch 1004, which may assist the patient 1002 to resolve such issues or discrepancies. To this end, the smart watch 1004 may acquire information of the patient 1002's surrounding in real-time. The information, for example, may include images of nearby objects and persons, a location information, sounds, and the like. Based on the real-time information, the smart watch 1004 may prompt the patient 1002 to perform one or more actions. To this end, the smart watch 1004 may utilize the acquired information of surrounding and the information elements of dependency tree 900 shown in the FIG. 9.

In the current exemplary embodiment, based on the acquired information, the smart watch 1004 may identify the current location of the patient 1002 as the swimming pool. Furthermore, the smart watch 1004 may extract the information elements associated with the place swimming pool from the dependency tree 900. In some embodiments, the acquired information may include sound of water and image of the swimming pool. Therefore, the node swimming pool 902 of the dependency tree may be accessed by the smart watch 1004.

As illustrated in FIG. 10, when the patient reaches the swimming pool, the smart watch 1004 may display a time 1004a, a location 1004b, instructor's image and voice 1004c, a first friend's image and voice 1004d, a second friend's image and voice 1004e, and the stuff required for swimming (such as, a swimming cap, swimming suit, and glasses). To display the information, the smart watch 1004 may have accessed the nodes 902, 904a, 904b, 904c, 906, 908, 910, 912, 914, and 916. In another example, the smart watch 1004 may provide a plurality of enquiry options to the patient 1002. Consider that the patient 1002 may choose an option "Where am I?". Then, the smart watch 1004 may identify the place as swimming pool and may extract the information associated with the swimming pool. The smart watch 1004 may provide assistance by displaying images, videos, text note or by a voice note. By way of an example, the smart watch 1004 may display a text note as "Hi John, this is your personal assistant. It is 5:00 PM. You are at the swimming pool. Here you may meet the instructor, and your friends Paul and Mary. Before entering into the swimming pool, you need to wear the swimming suit, the swimming cap and the swimming glasses that you may get from your bag."

Then, the smart watch 1004 may automatically generate a new text note or voice note, images, videos, at 6 PM, as swimming hours for the patient 1002 lapse at 6 PM. By way of an example, the text or voice note may be ""Hi John, this is your personal assistant. Uncle Robert is coming to pick you up at 6.00 PM with his car to take you home." Further, a picture of Robert, car, home, and location of home may also be displayed. It should be noted that voice of the assistant may be personalized with some other voice, for example with voice of John's parents.

Various embodiments provide method, system, and device for providing assistance to patients with communication and memory impairment. The disclosed method, system, and device may help to automate the process of providing assistance. The assistance providing device described in the present disclosure is portable and thus may be easily carried by a patient. By way of an example, the assistance providing device may be a smart watch, a smart phone, a tablet or the like. Further, the disclosed method, system, and device may specifically help people affected by Alzheimer by providing past information. Additionally, the disclosure may help autistic kids by providing relationships or actions to be performed sequentially based on an object or a specific place. Moreover, the disclosure is beneficial in terms of security, as the assistance providing device measures patient attributes and continuously monitors the patient and thereby prevents the patient from getting into a untoward or dangerous situation. To achieve this, the assistance providing device may alert the user when required and may also notify an authorized person immediately upon identification of any discrepancy.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Although the present invention has been described in connection with some embodiments, it is not intended to be limited to the specific form set forth herein. Rather, the scope of the present invention is limited only by the claims. Additionally, although a feature may appear to be described in connection with particular embodiments, one skilled in the art would recognize that various features of the described embodiments may be combined in accordance with the invention.

Furthermore, although individually listed, a plurality of means, elements or process steps may be implemented by, for example, a single unit or processor. Additionally, although individual features may be included in different claims, these may possibly be advantageously combined, and the inclusion in different claims does not imply that a combination of features is not feasible and/or advantageous. Also, the inclusion of a feature in one category of claims does not imply a limitation to this category, but rather the feature may be equally applicable to other claim categories, as appropriate.

What is claimed is:

1. A method for providing assistance to patients with communication and memory impairment, the method comprising:
    creating, by a relationship engine, based on a first set of information corresponding to a plurality of events associated with a patient, a database comprising: a plurality of information elements structured as a dependency tree,
        wherein each of the plurality of information elements is associated with at least one event of the plurality of events,
        wherein each of the plurality of information elements represent a first node of the dependency tree, and
        wherein the first node represents a location and is connected to a second node including different information elements associated with the patients;
    acquiring in real-time, via at least one of a plurality of sensors, a second set of information associated with the patient, after every predefined time interval;
    matching the second set of information with each of the plurality of events in the database to identify at least one matching event and with at least one information element associated with the at least one matching event at the second node to identify a set of matching information elements;
    determining, by the relationship engine, at least one new event and corresponding information elements in the second set of information based on the matching of the second set of information with each of the plurality of events in the database,
        wherein the at least one new event is absent from the database;
    comparing the second set of information with the set of matching information elements based on a predefined set of rules to identify at least one discrepancy, wherein the at least one discrepancy comprises at least one of deviation of the second set of information from a predefined series of steps associated with the at least one matching event of the plurality of events, and at least one anomaly in a plurality of patient attributes; and
    prompting the patient to perform at least one predetermined action in response to identifying at least one discrepancy;
    updating, by the relationship engine, the database based on the determined at least one new event,
        wherein the updating comprises creating, in the database, based on the second set of information, the at least one new event and at least one new dependency relationship based on the at least one new event and the corresponding at least one new information element; and
    validating the updated database by an authorized person, wherein the authorized person possesses the right to modify information in the database.

2. The method of claim 1, wherein creating the database further comprises:
    dynamically capturing a first subset of the first set of information via at least one of the plurality of sensors; and receiving a second subset of the first set of information from at least one authorised person associated with the patient.

3. The method of claim 1, wherein each of the first set of information and the second set of information comprises a video data, an audio data, and an image data associated with the patient, and wherein the plurality of events comprise at least one of an activity associated with the patient, an un-expected action performed by the patient, sudden change in usual behaviour of the patient, a proactive suggestion by the patient, a voluntary or involuntary action performed by the patient, absence of an action performed by the patient within a predefined time period, or an action performed by a person in vicinity of the patient.

4. The method of claim 1, wherein the plurality of sensors comprises at least one of a camera, a sound sensor, a proximity sensor, an Infra-Red (IR) sensor, a light sensor, an ultrasonic sensor, a temperature sensor, and pulse meter.

5. The method of claim 1, wherein the plurality of information elements in the database comprises at least one of an image of an object, event details, details associated with the object, time details, relation with a person, reference people in proximity for emergency condition, details of a person, an audio sound, a location, a name of the location, a video, and a phone number.

6. The method of claim 1, wherein creating the database comprises generating, via the relationship engine, the dependency tree comprising dependency amongst each of the plurality of information elements and with at least one of the plurality of events.

7. The method of claim 1, wherein prompting the patient to perform at least one predetermined action further comprises:
   sending a notification to the patient; and
   providing a plurality of sequential steps to be performed by the patient as the at least one predetermined action.

8. The method of claim 1, further comprising sending a notification to at least one authorized user in response to identifying the at least one discrepancy, wherein sending the notification comprises measuring the plurality of patient attributes comprising respiratory rate, heart rate, blood pressure, body gesture, and galvanic skin response of the patient.

9. An assistance providing device for patients with communication and memory impairment, the device comprising:
   a processor; and
   a memory communicatively coupled to the processor, wherein the memory stores processor-executable instructions, which, on execution, causes the processor to:
      create, based on a first set of information corresponding to a plurality of events associated with a patient, a database comprising a plurality of information elements structured as a dependency tree,
         wherein each of the plurality of information elements is associated with at least one event of the plurality of events,
         wherein each of the plurality of information elements represent a first node of the dependency tree, and
         wherein the first node represents a location and is connected to a second node including different information elements associated with the patients;
      acquire in real-time, via at least one of a plurality of sensors, a second set of information associated with the patient, iteratively after every predefined time interval;
      match the second set of information with each of the plurality of events in the database to identify at least one matching event and with at least one information element associated with the at least one matching event at the second node to identify a set of matching information elements;
      determine at least one new event and corresponding information elements in the second set of information based on the matching of the second set of information with each of the plurality of events in the database, wherein a new event is absent from the database;
      compare the second set of information with the set of matching information elements based on a predefined set of rules to identify at least one discrepancy, wherein the at least one discrepancy comprises at least one of deviation of the second set of information from a predefined series of steps associated with the at least one matching event of the plurality of events, and at least one anomaly in a plurality of patient attributes; and
      prompting the patient to perform at least one predetermined action in response to identifying at least one discrepancy;
      update the database based on the determined at least one new event, wherein the updating comprises creating, in the database, based on the second set of information, the at least one new event and at least one new dependency relationship based on the at least one new event and the corresponding at least one new information element; and
      validate the updated database by an authorized person, wherein the authorized person possesses the right to modify information in the database.

10. The assistance providing device of claim 9, wherein the processor-executable instructions cause the processor to create the database by:
   dynamically capturing a first subset of the first set of information via at least one of the plurality of sensors; and receiving a second subset of the first set of information from at least one authorised person associated with the patient.

11. The assistance providing device of claim 9, wherein each of the first set of information and the second set of information comprises a video data, an audio data, and an image data associated with the patient, and wherein the plurality of events comprise at least one of an activity associated with the patient, an un-expected action performed by the patient, a sudden change in usual behaviour of the patient, a proactive suggestion by the patient, a voluntary or involuntary action performed by the patient, absence of an action performed by the patient within a predefined time period, or an action performed by a person in vicinity of the patient.

12. The assistance providing device of claim 9, wherein the plurality of sensors comprises at least one of a camera, a sound sensor, a proximity sensor, an Infra-Red (IR) sensor, a light sensor, an ultrasonic sensor, a temperature sensor, and pulse meter.

13. The assistance providing device of claim 9, wherein the plurality of information elements in the database comprises at least one of an image of an object, details associated with the object, event details, time details, relation with a person, reference people in proximity for emergency condition, details of a person, an audio sound, a location, a name of the location, a video, and a phone number.

14. The assistance providing device of claim 9, wherein the processor-executable instructions further cause the processor to generate the dependency tree comprising dependency amongst each of the plurality of information elements and with at least one of the plurality of events via a relationship engine.

15. The assistance providing device of claim 9, wherein the processor-executable instructions further cause the processor to:

send a notification to the patient; and provide a plurality of sequential steps to be performed by the patient as the at least one predetermined action.

16. The assistance providing device of claim 9, wherein the processor-executable instructions further cause the processor to send a notification to at least one authorized user in response to identifying the at least one discrepancy, wherein sending the notification comprises measuring the plurality of patient attributes comprising respiratory rate, heart rate, blood pressure, body gesture, and galvanic skin response of the patient.

17. The method of claim 1, further comprising:
measuring the plurality of patient attributes in real time using the plurality of sensors to detect the at least one anomaly in the plurality of patient attributes;
identifying an atypical situation based on the at least one anomaly, wherein the atypical situation comprises panic-stricken patient, hiccups, sighs, and running patient; and
rendering a warning notification to the at least one patient and an authorized person associated with the at least one patient, based on the atypical situation.

\* \* \* \* \*